United States Patent
Gonzalez de la Rosa

(10) Patent No.: US 10,143,367 B2
(45) Date of Patent: Dec. 4, 2018

(54) INSTRUMENT AND METHOD FOR VISUAL FIELD EXAMINATION

(71) Applicant: INSTRUMENTACION Y OFTALMOLOGIA INSOFT S.L., Santa Cruz de Tenerife (ES)

(72) Inventor: Manuel Antonio Gonzalez de la Rosa, Santa Cruz de Tenerife (ES)

(73) Assignee: INSTRUMENTACION Y OFTALMOLOGIA INSOFT S.L., Santa Cruz de Tenerife (ES)

( * ) Notice: Subject to any disclaimer, the term of this patent is extended or adjusted under 35 U.S.C. 154(b) by 83 days.

(21) Appl. No.: 15/591,522

(22) Filed: May 10, 2017

(65) Prior Publication Data

US 2017/0325677 A1    Nov. 16, 2017

(30) Foreign Application Priority Data

May 10, 2016    (DE) .................. 10 2016 005 703

(51) Int. Cl.
  *A61B 3/02*    (2006.01)
  *A61B 3/00*    (2006.01)
  *A61B 3/024*   (2006.01)
  *A61B 3/18*    (2006.01)

(52) U.S. Cl.
  CPC ............. *A61B 3/024* (2013.01); *A61B 3/18* (2013.01)

(58) Field of Classification Search
  CPC . G02B 6/1226; G02B 27/46; G02F 1/133504; G02F 1/133711; A61B 3/024; A61B 3/032; A61B 3/18; A61B 2560/0406; A61B 5/103; A61B 5/1076; A61B 5/4393; A61H 19/34; A61H 19/44; A61H 2201/5048; A61H 2201/5058; A61H 2201/5061; A61H 2201/5064; A61H 2201/5079; A61H 2201/5084; A61H 2201/5097; A61H 23/0263
  USPC ........ 351/200, 203, 205, 208–210, 222–224, 351/245
  See application file for complete search history.

(56) References Cited

U.S. PATENT DOCUMENTS

2013/0148081 A1* 6/2013 Tanaka .................. A61B 3/102
                                                   351/206

\* cited by examiner

*Primary Examiner* — Brandi Thomas
(74) *Attorney, Agent, or Firm* — Hayes Soloway PC

(57) ABSTRACT

This document discloses both a method for visual field examination that makes it possible to perform eye sensitivity examinations and an instrument that is configured to perform said method for visual field examination. The method is based on absolute conditions, i.e. absolute differences in the differential luminous thresholds between symmetrical points with respect to the vertical meridian or the horizontal meridian are used; in this way, unlike with already-known methods, it is possible to study the symmetry and/or the harmony of the subjects themselves, without having to compare them to a reference population with all that this entails.

12 Claims, 4 Drawing Sheets

INSTRUMENT AND METHOD FOR VISUAL FIELD EXAMINATION

OBJECT OF THE INVENTION

The invention is framed within the field of optical and ophthalmic instruments.

More specifically, the invention relates to an instrument for visual field examination, as well as to a method that uses it.

BACKGROUND OF THE INVENTION

Campimetry is the study of the visual field for the detection of defects thereof (such as scotomas or areas with partial or total loss of vision) by means of an instrument called campimeter or perimeter. The visual field is defined as the space wherein an object may be seen whilst the eyes of the person under study are fixed forward.

There are different methods for studying the visual field; depending on the type of technique or perimeter used and the information obtained from them, perimetry may be classified into:

Qualitative campimetry: amongst them, the most widely used is confrontation perimetry: a basic, simple technique performed by the professionals themselves without the need for specific equipment (perimeter) which only provides basic information as to whether or not there is a visual field defect. It is used as a screening test.

Quantitative campimetry: It uses more complex techniques that require specific equipment (perimeter); amongst them, the most widely used are kinetic perimetry, manual or computerised (wherein the perimeter emits moving luminous stimuli, all at the same intensity) and static perimetry, manual or computerised (wherein the perimeter emits stationary luminous stimuli at different intensities and different locations); depending on the number and the location of the luminous stimuli that the patients recognise, or fail to, visual field maps are drawn which make it possible to identify non-seeing areas or areas with abnormal visual sensitivity (scotomas), and to exactly determine the size, the location and the depth of the scotoma area.

In confrontation perimetry, the patients remain seated in front of the examiner. Both eyes are examined independently; to do so, the patients must close one eye and stare at the examiner's opposite eye whilst the latter asks them to indicate when they see and/or cease to see an object that moves between both of them, throughout the visual field of the examined eye. Subsequently, the same operation is repeated with the fellow eye.

In kinetic perimetry, the patients remain seated in front of the perimeter. Both eyes are examined independently; to do so, the patients must close one eye whilst the examiner asks them to indicate when they see and when they cease to see a luminous beam that moves throughout the visual field of the eye under study. Subsequently, the same operation is repeated with the fellow eye.

In static perimetry, the patients remain seated in front of the perimeter and both eyes are examined independently; to do so, the patients must close one eye whilst the examiner asks them to indicate when they see a flashing luminous beam, at different intensities, that appears in different areas of the visual field of the eye under study. Subsequently, the same operation is repeated with the fellow eye. The most habitual way to examine the visual field is to determine the weakest luminous stimulus that the eye is able to perceive in each region, when presented over a uniformly illuminated background (differential luminous threshold).

In order to estimate the normality or abnormality of the result, the instrument usually has age-adjusted normative reference values from the normal population, examined in the same manner. The examination result is shown as absolute differential sensitivity values on a logarithmic scale (decibels) or as the difference between these values and the reference values (deviations or defects). Two of the most prestigious indices used to indicate the condition of the visual field are the mean defect or deviation of the points examined, measured as a mean (MD), and the irregularity, measured as the variance or standard deviation of the local defects or deviations (Pattern Standard Deviation, PSD, or Loss Variance, LV).

However, the fact that subjects present values that are distant from the habitual mean values does not guarantee that they are abnormal. For example, a subject may have an extremely low or high value with respect to a reference population and still be normal. Moreover, the fact that subjects fall within the habitual mean values does not guarantee that they are normal. For example, a subject may have a normal weight and have suffered an abnormal weight loss. Our experience indicates that, in these cases, harmony can be an excellent indicator of normality.

On the other hand, it is well-known that keeping the eye observing a uniformly illuminated surface during the examination, without any other contrast phenomena than those of the examination stimulus, is contrary to the physiology of vision, wherein changes in contrast are necessary in order to "refresh" the functioning of the retina. This produces a progressive reduction in sensitivity, which we call "fatigue effect", to refer to a fatigue of the neurological mechanisms of vision, which distorts the patients' actual functional capacity. In order to reduce this undesired phenomenon, our system periodically presents a rapid sequence of figures with random contrasts and shapes, in the form of short flashes interspersed between the examination periods.

DESCRIPTION OF THE INVENTION

One aspect of the invention relates to an instrument designed to perform visual field examinations, which is presented with a given form of photometric control. The instrument of the invention is especially indicated for the method for visual field examination that is another aspect of the invention, which makes it possible to quickly estimate the visual field sensitivity, and may use several circles to ensure a correct position of the eye in subjects with poor central vision; this is especially designed to study the symmetry and the harmony of the visual field, which may be used as a diagnostic index, regardless of the mean values in the normal reference population or jointly with them, since this association may enhance the diagnostic capacity of both parameters in a single index or indicator, thereby involving greater efficacy and allowing for a better diagnosis.

The instrument of the invention is similar to that habitually used to examine the visual field, the so-called perimeter or campimeter. It consists of a flat or curved screen that emits or reflects daytime-type light (photopic environment), which virtually simulates the visual field of the subject being examined. Over this background, luminous stimuli of known contrast are generated, on a logarithmic scale (decibels), which make it possible to study the aforementioned "differential luminous threshold".

In most conventional perimeters, the stimulus and the background are projected onto a dome using two different light sources and the patients observe the light reflected or emitted towards the eye. In these instruments, the background illumination is habitually performed from a lateral position, which results in a relative lack of uniformity and, consequently, in regional differences in the test contrast with respect to the background.

The background illumination is habitually performed at a level of 31.5 apostilbes or asb (10 candelas/m$^2$), and the luminance scale of the stimuli is calibrated with respect to it. Level 0 of the logarithmic scale of the stimuli is established with respect to that of the maximum luminous intensity. For example, a maximum stimulus of 10000 asb will define the value of 0 dB on the perimeter scale, since:

$$-10x\log(10000/31.5)/(10000/31.5) =$$
$$-10x\log(317.5/317.5) = -10x\log(1) = 0 \text{ dB}$$

The remaining levels of the scale are defined by stimuli the contrast whereof with respect to the background and the maximum value provide approximately integer values on this logarithmic scale. For example, a stimulus with an intensity of 100 asb will define the 20-dB level of the scale, since:

$$-10x\log(100/31.5)/(10000/31.5) =$$
$$-10x\log(3.175/317.5) = -10x\log(0.01) = 20 \text{ dB}$$

Although the examination method of the object of the invention may be implemented using a conventional perimeter, it is optimal to apply it using an instrument that directly calibrates the contrast levels, as in the case of the instrument of the invention, and not the absolute background and stimulus luminances. Application of said calibration will allow for higher precision in the biological parameter to be measured and for greater stability in the results, which will facilitate estimating the symmetry and/or the harmony.

In order to achieve this, it is optimal that the calibration process be implemented using the same light source and projection direction to generate both the stimulus and the background; for example, using a computer monitor, a mobile telephone screen, a virtual reality helmet, a digital image projector, etc. Using a daytime-level background illumination (photopic environment), a change in the stimulus with a magnitude proportional to a simultaneous change in the background will provide the same contrast and, therefore, an equivalent visual sensation (Weber-Fechner Law).

The 0-dB stimulus may be obtained by projecting 10031.5 asb from a region of the illumination plane, whereas the rest of the screen projects 31.5, since:

(10031.5−31.5)/31.5=10000/31.5=317.5

But also, for example, from a region that projects 12738.4 asb towards the eye, whilst the rest of the screen projects 40 asb, since the differential luminosity quotient will be:

(12738.4−40)/40=12698.4/40=317.5

Although a system of this type may present slight absolute differences in surface illumination, these will proportionally affect the stimuli and the background, fulfilling the Weber-Fechner Law, and providing greater contrast stability than with the habitual double-illumination instruments, which allows for stable adjustment without the need for permanent photometric control.

Thus, when the instrument is calibrated, even if there are small changes with time, for example, due to ageing or temperature differences, the instrument will keep the test/background contrast quotients sufficiently constant throughout the necessary scale.

In the prior art, it has been proposed to analyse the symmetry between the upper or lower visual fields, by making a mirrored comparison of the deviation values in each region with respect to the normal population. However, in the object of the invention, the absolute differences in the differential luminous thresholds are calculated between symmetrical points with respect to the vertical meridian or the horizontal meridian. In this way, the symmetry and the harmony of the subjects are studied in themselves, without comparing them to a reference population. It is also worth noting that different statistical parameters, such as the mean of the absolute differences in the thresholds, their median, their variance, or Pearson's coefficient of variation may be used directly as diagnostic indices, or be associated with traditional results (mean defect or deviation, MD; Pattern Standard Deviation, PSD; or Loss Variance, LV), in order to generate a single index that encompasses the individuals' own asymmetry and their differences with respect to the standard normative basis.

The object of the invention may be implemented using a virtual reality device, such as virtual reality helmets, which allow for two screens, or two portions of the same screen, to be perceived independently by both eyes, simultaneously or in quick alternation, which allows for the simultaneous examination of both eyes, and not consecutive examination, as has been done thus far, nonetheless obtaining independent results for each. In the case of monocular visual field defects, using the virtual reality helmet or equivalent device, wherein two screens or two portions of the same screen are perceived independently by both eyes, simultaneously or in quick alternation, makes it possible to keep the eye with the central defect that is to be examined focused, by keeping the opposite eye fixed on the fixation point of the other screen. Moreover, the implementation of the object of the invention in virtual reality devices, wherein the two screens or two portions of the same screen are perceived independently by both eyes, simultaneously or in quick alternation, makes it possible to simultaneously examine equivalent points in the visual field of both eyes in order to analyse their possible asymmetry and harmony, and use them as a diagnostic index.

Other objects of the invention are a computer program comprised within a support, with the necessary instructions for a processing unit to perform the method for visual field examination of the invention, and the instrument for visual field examination adapted to perform the method of the invention, which uses a processing unit and at least data storage means that comprise the aforementioned computer program.

DESCRIPTION OF THE DRAWINGS

In order to supplement the description being made, and to contribute to a better understanding of the characteristics of the invention, according to a preferred embodiment thereof, a set of drawings is attached to said description as an integral part thereof, where the following is represented for illustrative, non-limiting purposes.

PREFERRED EMBODIMENT OF THE INVENTION

A first aspect of the object of the invention relates to a method for examining a person's visual capacities. To this end, a device such as the one disclosed in the second aspect of the invention may be used, although a standard device configured as such may be used to implement said method.

Using the device of the second aspect of the invention is recommended due to the fact that it is necessary to have an instrument that is calibrated as indicated above; moreover, an essential condition in order to precisely measure the sensitivity of the eye is quickness, since the retina progressively loses its function when it is subjected to the uniform contrast conditions necessary for the visual field examination. For this reason, the method of the invention may start with a short training period, which, at the same time, makes it possible to detect severe defects.

The method comprises subsequently obtaining, within a time interval of approximately one minute, basic information about the normality or the pathology of the visual field, by examining a limited number of representative symmetrical points. This basic information, which is very close to the final result, also serves as a starting-point to refine the sensitivity estimates, by successively examining groups of points that are also symmetrically located with respect to the centre of the visual field. Each phase makes it possible to successively improve the sensitivity estimates for the entire visual field, until precise results, with small fluctuations, are obtained, within a total time ranging between 2 and 4 minutes.

Figures 1, 2:
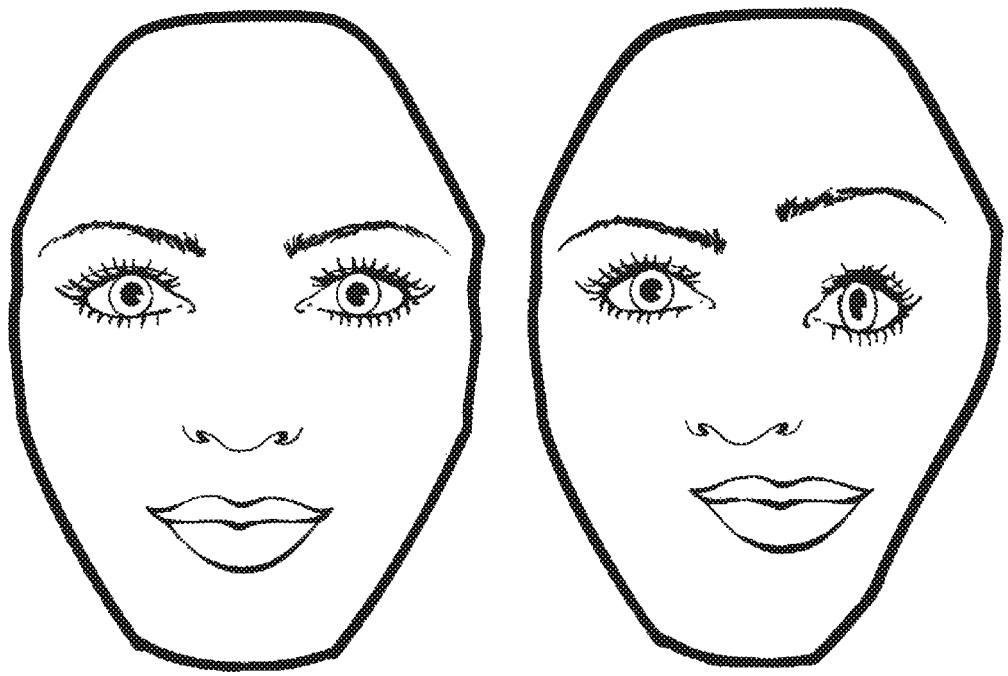
FIG. 1.—Shows two images wherein we may observe a first captured image that is symmetrical and harmonious, whereas the second image presents asymmetry and does not present harmony.
FIG. 2.—Shows a possible distribution of the examination points of the method of the invention.

As may be observed in FIG. 2, the visual field is divided into examination points grouped into symmetrical sets. In this example, the points are distributed into rows and columns separated by 6 degrees with respect to the central fixation point, although another type of distribution may be used.

In a first phase of the method of the invention, the sensitivity of the eye is examined with respect to a first set of points corresponding to the beginning of the arrangement sequence, i.e. the points indicated with Number 1 are examined several times using a relatively high luminance contrast, which any normal subject should perceive, to obtain a first response (seen or not seen), Tc. Thus, the subjects understand what is expected of them, their level of collaboration is determined, and the presence of severe defects in the four quadrants of the visual field (upper and lower nasal, and upper and lower temporal) is confirmed or discarded.

Subsequently, a second phase is performed wherein the sensitivity of the eye is examined with respect to a second set of examination points corresponding to the positions immediately following the first points; i.e. in view of FIG. 2, the points indicated with Number 2 are examined with a supraliminal contrast, which has a value that is slightly higher than the normal sensitivity value for the normal population of the same age (suprathreshold stimulus), to obtain a second response (seen or not seen), Ta, Tb, Td, Te.

Figure 3:
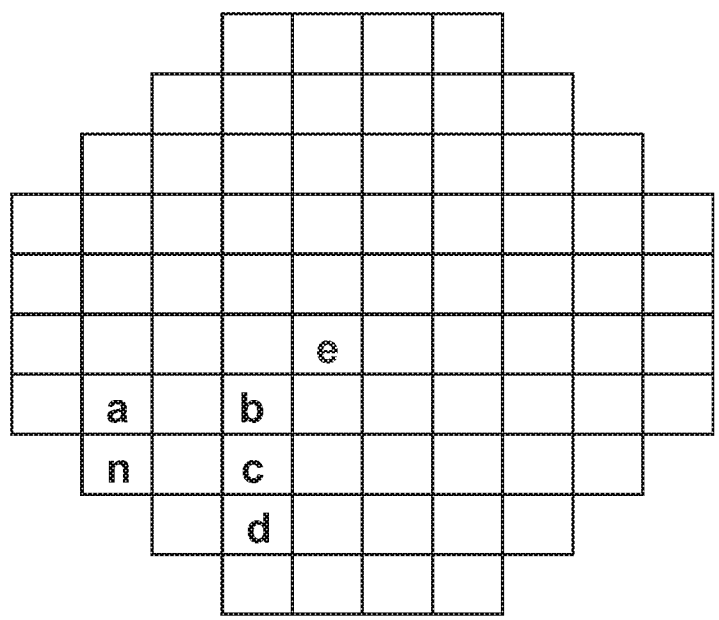
FIG. 3.—Shows an illustration of the estimated sensitivity of points not examined.

The results of the first and second phases make it possible to perform an approximate estimate of the sensitivities of the points not examined, on the basis of equations that have been obtained following the analysis of over 50,000 normal and pathological visual fields. FIG. 3 shows a possible way to perform said estimate, since it approximately illustrates one of these equations, wherein, once the responses (T) at some of the first and second sets of points, for example, Ta, Tb, Tc, Td, Te, have been obtained as explained above, the probable deviation of another point, for example point X, may be estimated using the formula:

$$Tn = -22 + 5Ta + 3Tb + 11Tc + 4Td + 1Te$$

A formula may be used that is selected from a set of formulas based on clinical observations; such a set of equations makes it possible to perform a first estimate of the sensitivities of the entire visual field, with which the examination continues; the responses to the first and second series of points (Tc and Ta, Tc, Td, Te) are used to estimate the threshold of all the points by means of a set of equations, the results whereof are used to continue the examination.

On the basis of the responses to the first and second series of points, in this case those corresponding to Tc and Ta, Tb, Td, Te, a set of equations such as the one specified, or a similar one, makes it possible to perform a first estimate of the deviations in the entire visual field. The deviations are equivalent to a given threshold or sensitivity according to the age of the subject, and this threshold estimate is used to continue the examination.

In the next phase of the method, the sensitivity of the eye is examined with respect to a third set of symmetrical points, corresponding to the positions immediately following the second set of points in the arrangement sequence, using the luminance contrast corresponding to the threshold estimated in the preceding phase; i.e. in view of FIG. 2, those symmetrical points indicated with Number 3 are examined, using stimuli in accordance with the sensitivity results estimated in the preceding phase. Once this phase has been completed, a new estimate of all the points in the visual field may be performed, on the basis of their proximity to those examined. This new estimate is used to select the adequate contrast of the stimuli with which the symmetrical points in a new subsequent phase will be examined; this phase will likewise be continued with another subsequent phase, at the end of which the final result will be reached. In this example, there are five phases corresponding to the five aforementioned groups of points. In the event that there are more or less points, the number of phases also varies, but the process always has the same beginning and a number of points/phases not less than two.

The point distribution may be modified by eliminating rows or columns, or other point distributions may be used that follow a similar idea, but they must always be symmetrical distributions.

Figure 4:
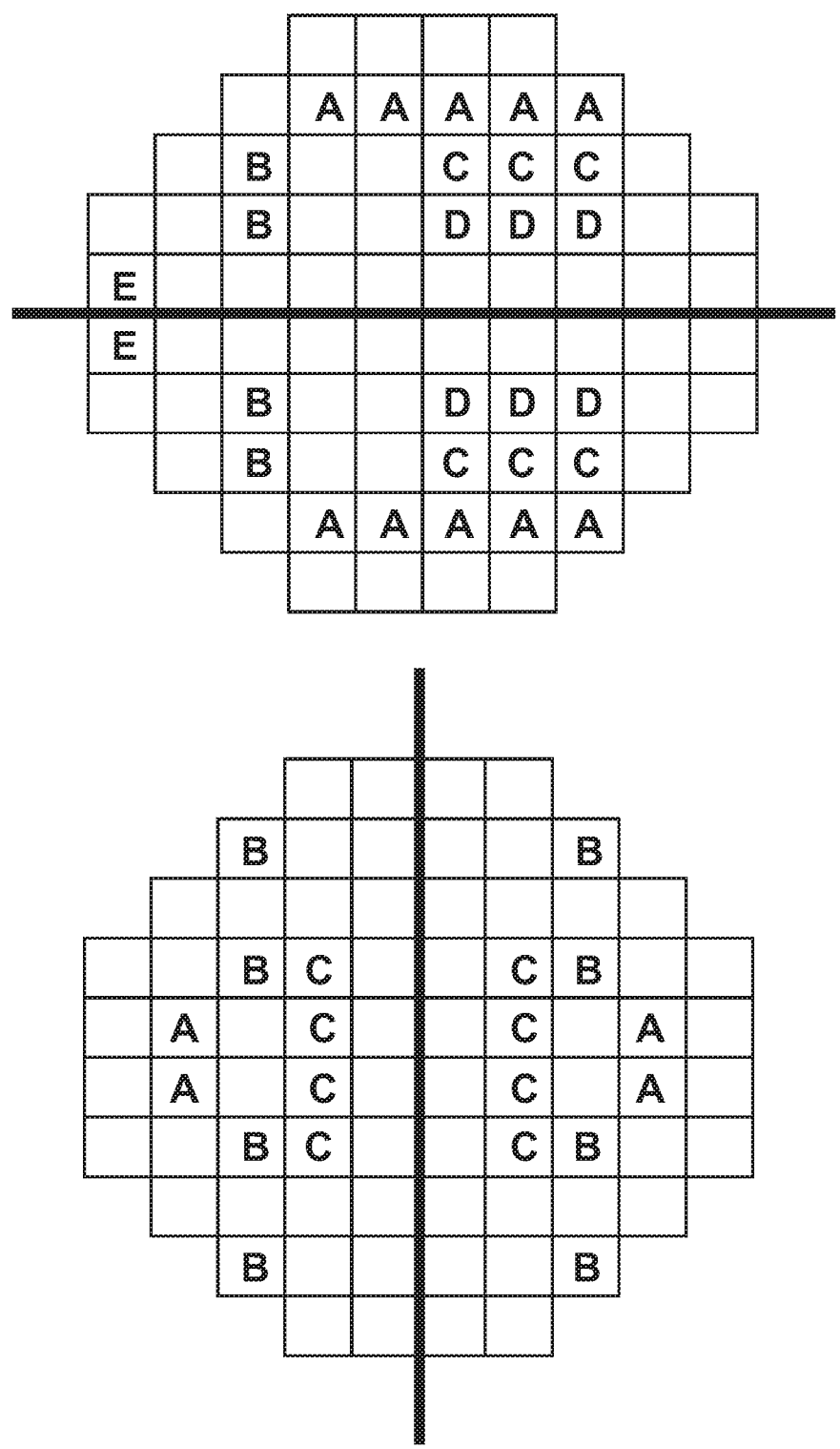
FIG. 4.—Shows an illustration that represents an example of points with vertical and horizontal symmetry.

The method of the invention makes it possible to calculate absolute differences in the differential luminous thresholds between symmetrical points with respect to the vertical meridian or the horizontal meridian. As indicated above, this makes it possible to study the symmetry and the harmony of subjects themselves, without comparing them to a reference population. In order to perform said calculation, once the sensitivity thresholds have been estimated by means of the method of the invention described above, the absolute differences between the thresholds of points located at specular positions with respect to these meridians are calculated. FIG. 4 shows an example of points with vertical and horizontal symmetry, which are useful for the diagnosis of glaucoma, for a visual field of the right eye. The selected points may be modified depending on the pathology investigated or the distribution of the points examined.

In a possible alternative embodiment of the method of the invention, the so-called fatigue effect, which arises from keeping the eye observing a uniformly illuminated surface during the examination, without any other contrast phenomena than those of the examination stimulus, is taken into consideration. This situation is contrary to the physiology of vision, wherein changes in contrast are necessary to "refresh" the functioning of the retina. This produces a progressive reduction in sensitivity which we call "fatigue effect", to refer to a fatigue of the neurological mechanisms of vision, which distorts the patients' actual functional capacity. In order to reduce this undesired phenomenon, the method of the invention comprises performing a periodical presentation, throughout the entire surface of the screen, of a quick sequence of figures with random contrasts and shapes, in the form of short flashes interspersed between the examination periods.

Figure 5:
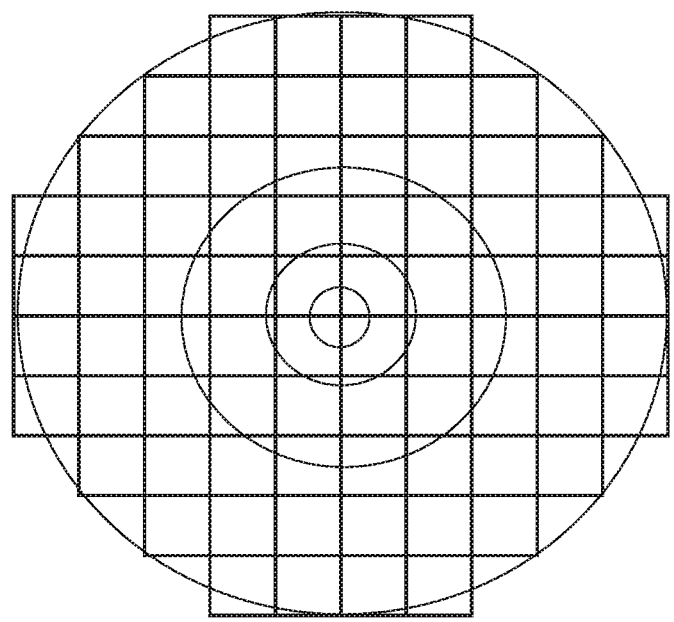
FIG. 5.—Shows an illustration that represents an example of the use of fixation circles for patients with central vision defects.

In possible, even more alternative embodiments, when the patients have central vision defects, the central luminous points whereon the patients are habitually told to keep their eyes fixed during the examination may be replaced with luminous circles that do not coincide with the points to be examined, such that the subjects may imagine the position of their geometric centre, as may be observed in FIG. 5, which will facilitate a correct positioning of the eye, even when the central vision is deficient.

The invention claimed is:

1. Method for visual field examination characterised in that it comprises:
   i. dividing the visual field into examination points grouped into symmetrical sets, wherein the examination points are sequentially arranged,
   ii. examining the sensitivity of the eye with respect to a first set of points corresponding to the beginning of the arrangement sequence, using a relatively high luminance contrast that any normal subject should perceive, to obtain a first response Tc,
   iii. examining the sensitivity of the eye with respect to a second set of symmetrical examination points, corresponding to the positions immediately following the first set of points in the arrangement sequence, using a supraliminal luminance contrast corresponding to a luminance contrast value that is slightly higher than a normal sensitivity value for a population without vision defects of the same age as that of the subject under examination, to obtain a second response, Ta, Tb, Td, Te,
   iv. performing a response estimate Tn corresponding to each of the remaining examination points in the visual field, on the basis of their proximity to those examined, using a set of formulas based on clinical observations, in order to select an adequate luminance contrast of the stimuli, and
   v. performing a number of sensitivity examinations of the eye equal to the remaining examination points, such that each of said examinations is performed using the adequate luminance contrast of stimuli estimated in the preceding step.

2. Method for visual field examination according to claim 1, wherein the visual field is divided by means of a symmetrical distribution of the examination points.

3. Method for visual field examination according to claim 1, wherein the visual field is divided by means of a symmetrical distribution of the examination points into rows and columns, with a separation of 6 degrees with respect to a central fixation point.

4. Method for visual field examination according to claim 1, wherein the sequence of the examination points increases with respect to the central fixation point.

5. Method for visual field examination according to claim 1, wherein the threshold deviations of the points not examined are estimated by applying formulas of the following type:

$$Tn=-22+5Ta+3Tb+11Tc+4Td+1Te$$

where Tn is a deviation value at a point not examined and Ta, Tb, Tc, Td, Te are responses to the stimuli presented at the points corresponding to the T positions in the arrangement sequence.

6. Method for visual field examination according to claim 1, further comprising periodically presenting, throughout the entire surface of the screen, a quick sequence of figures with random contrasts and shapes, in the form of short flashes interspersed between the examination periods.

7. Method for visual field examination according to claim 1, further comprising calculating absolute differences between the thresholds of points located at specular positions with respect to at least one horizontal or vertical meridian that defines appropriate symmetry.

8. Method for visual field examination according to claim 1, further comprising generating luminous circles that do not coincide with the points to be examined, such that the subjects may imagine the position of their geometric centre.

9. Computer program comprised within a support, characterised in that it comprises the necessary instructions for a processing unit to perform the method for visual field examination according to any of the preceding claims.

10. Instrument for visual field examination characterised in that it is adapted to:
   directly calibrate contrast levels and not absolute background and stimulus luminances, and
   perform the method of claims 1 to 8.

11. Instrument for visual field examination comprising a processing unit and at least data storage means that comprise the computer program of claim 9.

12. Instrument according to claim 10, comprising a virtual reality device equipped with a screen divided into two parts or two screens, such that they are perceived independently by both eyes.

* * * * *